(12) United States Patent
Blondeau

(10) Patent No.: US 8,177,916 B2
(45) Date of Patent: May 15, 2012

(54) FRAGRANCE DISSEMINATION DEVICE

(75) Inventor: Philippe Blondeau, Paris (FR)

(73) Assignee: Givaudan S.A., Vernier (CH)

( * ) Notice: Subject to any disclaimer, the term of this patent is extended or adjusted under 35 U.S.C. 154(b) by 315 days.

(21) Appl. No.: 12/598,854

(22) PCT Filed: May 20, 2008

(86) PCT No.: PCT/CH2008/000227
§ 371 (c)(1),
(2), (4) Date: Nov. 4, 2009

(87) PCT Pub. No.: WO2008/141473
PCT Pub. Date: Nov. 27, 2008

(65) Prior Publication Data
US 2010/0132743 A1    Jun. 3, 2010

(30) Foreign Application Priority Data

May 23, 2007 (EP) .................................. 07290659

(51) Int. Cl.
*B08B 7/00* (2006.01)
*A61L 9/00* (2006.01)
*A61L 9/04* (2006.01)

(52) U.S. Cl. ......... 134/25.2; 134/18; 134/42; 134/56 D; 422/5; 424/76.3; 424/76.4; 239/34; 239/60

(58) Field of Classification Search ................ None
See application file for complete search history.

(56) References Cited

U.S. PATENT DOCUMENTS 4,545,917 A * 10/1985 Smith et al. .................. 510/224

| 7,528,102 B2 | 5/2009 | Barthel et al. |
| 2005/0148479 A1* | 7/2005 | Barthel et al. ............. 510/101 |
| 2008/0011870 A1 | 1/2008 | Link et al. |
| 2009/0088357 A1 | 4/2009 | Huppert et al. |

FOREIGN PATENT DOCUMENTS

DE    10 2005 025041 A1    12/2006
(Continued)

OTHER PUBLICATIONS

PCT/CH2008/000227—Written Opinion of the International Searching Authority, Jul. 21, 2008.
(Continued)

*Primary Examiner* — Michael Kornakov
*Assistant Examiner* — Nicole Blan
(74) *Attorney, Agent, or Firm* — Curatolo Sidoti Co, LPA; Joseph G. Curatolo; Salvatore A. Sidoti

(57) ABSTRACT

A malodour-counteracting device adapted to be used in an automatic dishwasher having at least one washing cycle and a final drying cycle, the device having the form of two connected containers, adapted to rest on a horizontal surface within the dishwasher to provide an upper container (2) and a lower container (1), the lower container having the form of an open dish and the upper container, within which is a gradually-releasable evaporable malodour counteractant (6), fitting within the lower container and providing at least one port (3) permitting the passage of malodour counteractant out of the upper container, the lower container being adapted, during the washing cycle, to contain sufficient water to submerge the port, and during the drying cycle to allow the port to be open. The device is easy and cheap to manufacture, and is effective for a prolonged period.

4 Claims, 1 Drawing Sheet

FOREIGN PATENT DOCUMENTS

| | | | |
|---|---|---|---|
| FR | 2547733 | A | 12/1984 |
| GB | 2413262 | A | 10/2005 |
| WO | WO 2005/102141 | A | 11/2005 |
| WO | WO 2005102141 | A1 * | 11/2005 |

OTHER PUBLICATIONS

PCT/CH2008/000227—International Search Report, Jul. 21, 2008.

GB 0716008.8—Great Britain Search Report, Dec. 13, 2007.

* cited by examiner

FRAGRANCE DISSEMINATION DEVICE

CROSS REFERENCE TO RELATED APPLICATIONS

This application is a national stage application of International Application No. PCT/CH2008/000227, filed 20 May 2008, which claims the benefit of European Patent Application Serial No. EP 07290659.7, filed 23 May 2007, from which applications priority is claimed, and which are incorporated herein by reference.

This invention relates to a method of disseminating fragrance in an automatic dishwasher, and to an apparatus for achieving this.

Deodorants and fragrances to counter malodour in automatic dishwashers are well known. They are present to counter malodours produced by the deposition of dirty dishes, kitchen utensils and cutlery in a dishwasher and leaving them there for an extended period without washing, as typically happens when the items to be washed do not constitute a full load and the owner does not want to waste water unnecessarily. A typical deodorant comprises fragrance adsorbed into a porous carrier such as plastic beads or a fragrance reservoir sealed with a permeable polyolefin membrane through which the fragrance diffusion takes place.

While this has been generally effective, it has a number of drawbacks. One of these is the increased evaporation of fragrance during the wash cycle, courtesy of elevated temperature, followed by a reduced evaporation in between washes. This between-washes time is often the time when more, rather than less, fragrance is needed, as dirty dishes and cutlery are, as mentioned hereinabove, often put into the dishwasher and left, becoming malodorous.

It has now been found that the disadvantages of current deodorant technologies can be substantially or even completely overcome. There is therefore provided a malodour-counteracting device adapted to be used in an automatic dishwasher having at least one washing cycle and a final drying cycle, the device having the form of two connected containers, adapted to rest on a horizontal surface within the dishwasher to provide an upper container and a lower container, the lower container having the form of an open dish and the upper container, within which is a gradually-releasable evaporable malodour counteractant, fitting within the lower container and providing at least one port permitting the passage of malodour counteractant out of the upper container during the final drying cycle, the lower container containing a port-submerging quantity of water during the washing cycle.

There is additionally provided a method of counteracting malodour in an automatic dishwasher containing unwashed dishes prior to at least one washing and a final drying cycle, comprising the provision on a horizontal surface within the dishwasher of a device having the form of two connected containers, to provide an upper container and a lower container, the lower container having the form of an open dish, and the upper container, within which is a gradually-releasable evaporable malodour counteractant, fitting within the lower container and providing at least one port permitting the passage of malodour counteractant out of the upper container, the lower container being adapted, during the washing cycle, to contain a port-submerging and malodour counteractant-retaining quantity of water, and, during the drying cycle, to provide an open and malodour counteractant-releasing port.

The device hereinabove defined comprises two containers, which are connected together. The connection can be by any suitable means, for example, bolts or other fastening elements, press-fit and adhesive. Alternatively, the containers may comprise a single unit formed by any suitable means, such as moulding or casting. The materials of the containers may be any materials suitable for the purpose, able to withstand the temperatures, exposure to water, abrasion and chemical attack encountered within a dishwasher. Typical materials include plastics such as polyethylene, polypropylene, PETG (polyethylene glycol terephthalate) and nylon, metals, such as aluminium, brass and stainless steel, and ceramics.

The containers are arranged such that, when in place on a horizontal surface in a dishwasher, one container is an upper container and the other a lower container. They are configured such that the upper container fits within the lower container, the latter having the form of an open dish. Provided that this is the case, the shapes and sizes of the containers are not critically important, other than the fact that they are suitably dimensioned and positioned to perform their function, as will be hereinafter described. Any suitable shapes may be chosen, and they need not be the same for both containers. One typical shape is cylindrical, with circular cross-sections, the upper container fitting within the lower container (not necessarily concentrically). However, any other desired cross-sectional shape is possible, for example, elliptical, square, rectangular and polygonal. It is also not necessary that either container be a cylinder. For example, one or both may be part-spherical, conical or pyramidal. The skilled person will be able to provide any suitable shape in any suitable dimension.

The upper container contains a malodour counteractant. This may be any suitable substance capable of evaporation and counteracting malodour. For example, it may be a fragrance, and any suitable known fragrance may be used. Alternatively, it may be a volatile chemical substance with no hedonistic odour of its own, but one that specifically interacts with malodour-causing substances, removing the malodour. Suitable fragrance materials include fragrance materials selected from such classes as acids, esters, alcohols, aldehydes, ketones, lactones, nitriles, ethers, acetates, hydrocarbons, sulfur- nitrogen- and oxygen-containing heterocyclic, polycyclic and macrocyclic compounds, as well essential oils of natural or synthetic origin. Such fragrance materials are described, for example, in S. Arctander, Perfume Flavors and Chemicals Vols. 1 and 2, Arctander, Montclair, N.J. USA 1969. The fragrance optionally may comprise odourless liquids such as benzyl benzoate, isopropylmyristate, and hydrocarbon derivatives, for example Isopar® from Exxon or glycol ethers from Dow Chemical.

The malodour counteractant is gradually releasable, that is, it is kept within the container in such a manner that it will be released over a prolonged time period. This can be achieved in any suitable manner, and the skilled person will readily be able to realize many suitable means of achieving this. Examples include absorption in a solid porous substance, incorporation into a gel and retention behind a membrane adapted to permit slow passage of the liquid and evaporation at the surface thereof.

In a particular embodiment, the malodour counteractant is refillable or replaceable. This is easily achieved, and the means for doing so depend on the nature of the individual device. In one particular embodiment, the upper container complete with malodour counteractant may be supplied as a replacement part. In another particular embodiment, the malodour counteractant may be supplied in a form that allows its easy replacement within the upper container. For example, the malodour counteractant may be contained in a unit that is equipped with screw threads or snap-fit elements that mate with corresponding elements in the upper container. Thus, when the malodour counteractant is exhausted, the exhausted unit may be replaced by a new unit.

The upper and lower containers are configured and arranged such that
(a) the upper container comprises at least one port through which malodour counteractant may be released:
(b) when there is a washing cycle, the lower container contains sufficient water to submerge the port, such that no malodour counteractant can exit therefrom; and
(c) during the final drying cycle, the port is no longer submerged and malodour counteractant can pass out of the upper container into the interior of the dishwasher.

The port through which the malodour counteractant is released may be any suitable opening. (Although referred to in the singular, there may be more than one such port, and the use of the singular herein refers also to the plural). Generally, it is positioned at the lower end of the upper container when the device is in place. It may be any suitable shape, or it may be provided in any manner. For example, the upper container may be a completely closed container with a suitably located port or slot. A further embodiment is an upper container completely open at the lower end, the opening through which the malodour counteractant is released being defined by an appropriate spacing of the upper container from the lower container, achieved by any convenient means.

The opening is located and the lower container is dimensioned so that, when there is a washing cycle, the port is submerged and no malodour counteractant can escape.

The achievement, during the drying cycle, of the opening of the port to allow malodour counteractant to escape may be achieved by any convenient means. In one particular embodiment, the opening is achieved by allowing the water to be evaporated during the drying cycle, such that the level of water in the lower container falls sufficiently to uncover the port. This can readily be achieved by the appropriate dimensioning of the containers and placement of the port.

In another embodiment, the lower container comprises a drain hole, through which water can escape. The location and size of this drain hole and the size and configuration of the lower container are such that water in the lower container takes a desired time to drain. The drain time is regulated such that malodour counteractant escapes into the interior of the dishwasher when the wash cycle has finished.

Thus, when dirty dishes are placed in a dishwasher, the malodour counteractant is emitted and counteracts any malodour caused by the dishes remaining unwashed therein for some time. When a wash is initiated, the lower container fills with water, and the malodour counteractant is trapped in the upper container, preserving it until the wash is finished. The malodour counteractant is therefore emitted only when needed and it therefore more effective for longer.

The device is easily and inexpensively manufactured from known materials using techniques well known to the art. It is effective in use in reducing malodours from dirty items left in a dishwasher for a prolonged period prior to washing, so that it is possible to do this without detriment to the environment in which the dishwasher is located. Depending on the nature of the particular device, it can be easily replaced or refilled.

The invention is now further described with reference to the accompanying drawing, which depicts a preferred embodiment, and which is not intended to be in any way limiting on the scope of the invention.

Figure 1:
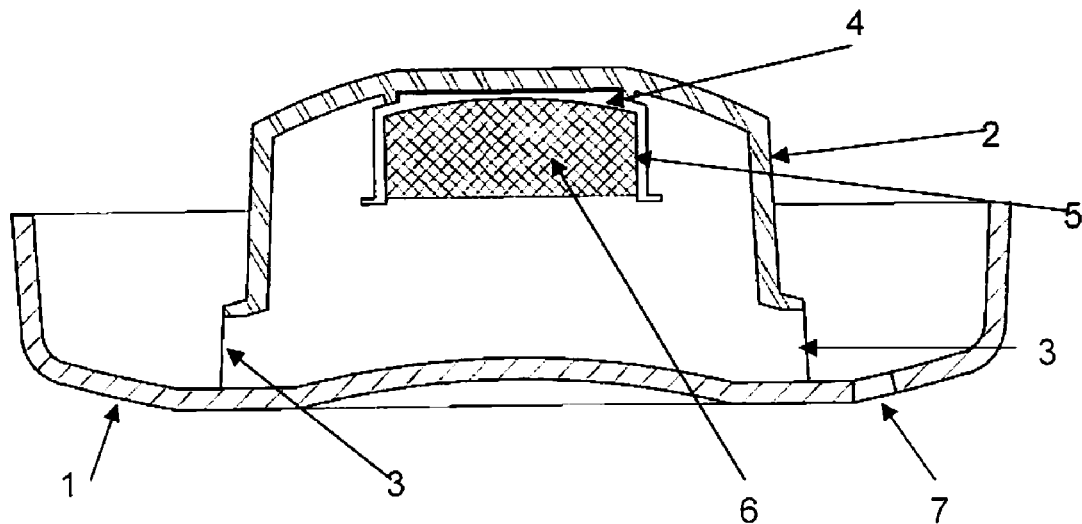
FIG. 1 depicts a schematic vertical cross-section through an embodiment mounted in an automatic dishwasher, when there is no water in the dishwasher.
Figure 2:
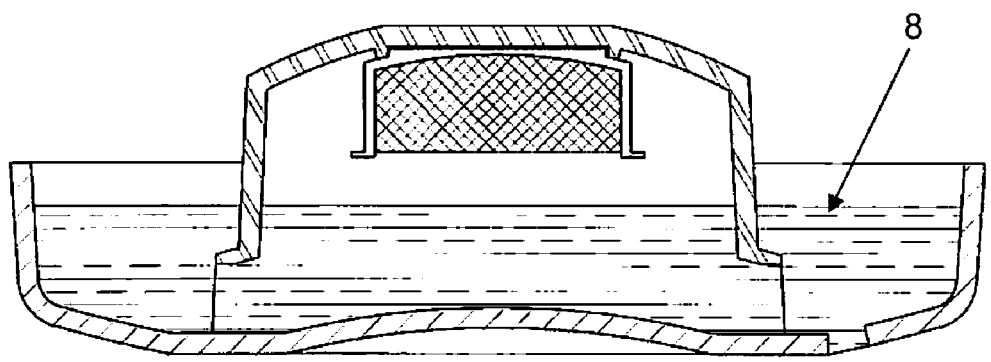
FIG. 2 depicts the embodiment of FIG. 1 during a washing cycle.

The embodiment of FIGS. 1 and 2 has the form of a shallow dish 1, which is adhered a horizontal internal surface of a dishwasher. Releasably mounted on this dish by means of cooperating screw threads (not shown) is a fragrance holder 2 having the form of an inverted cup. Both are made from plastics. Where the rim of this cup meets the dish there are a number of cut-outs, which define a series of ports 3, which allow air within the fragrance holder to escape into the interior of the dishwasher. Releasably mounted on the internal base of the cup by means of a snap fitting 4 is a reservoir 5 containing a malodour counteractant-containing gel 6.

The dish 1 has a drain hole 7, so that water therein may escape.

In operation, the dish fills with water 8, as shown in FIG. 2. When this happens, the ports 3 are submerged and malodour counteractant from the gel 6 is trapped in the cup 2. The drain hole 7 is of such a size that the water drains relatively slowly from the dish (the hole is of such a dimension in relation to the size of the dish that a desired drain time is achieved). Thus, when the machine is in operation, the malodour counteractant cannot escape and is preserved until the ports are clear of water. The malodour counteractant can then escape into the interior of the dishwasher.

When the malodour counteractant is exhausted, the cup can be unscrewed from the dish, the exhausted reservoir removed and a new one snapped into place.

The skilled person will appreciate that there are many embodiments that fall within the scope of this description that can be easily realized by the exercise of the ordinary skill of the art.

The invention claimed is:

1. A malodour-counteracting device adapted to be used in an automatic dishwasher having at least one washing cycle and a final drying cycle, the device having the form of two connected containers, adapted to rest on a horizontal surface within the dishwasher to provide an upper container and a lower container, the lower container having the form of an open dish and the upper container, within which is a gradually-releasable evaporable malodour counteractant, fitting within the lower container and providing at least one port permitting the passage of malodour counteractant out of the upper container during the final drying cycle, the lower container containing a port-submerging quantity of water during the washing cycle.

2. A device according to claim 1, in which the lower container and the port are so configured that the port is opened by the evaporation of water.

3. A device according to claim 1, in which the lower container comprises a drain hole through which water can escape, the location and size of this drain hole and the size and configuration of the lower container being such that water in the lower container takes a desired time to drain.

4. A method of counteracting malodour in an automatic dishwasher containing unwashed dishes prior to at least one washing and a final drying cycle, comprising the provision on a horizontal surface within the dishwasher of a device having the form of two connected containers, to provide an upper container and a lower container, the lower container having the form of an open dish, and the upper container, within which is a gradually-releasable evaporable malodour counteractant, fitting within the lower container and providing at least one port permitting the passage of malodour counteractant out of the upper container, the lower container being adapted, during the washing cycle, to contain a port-submerging and malodour counteractant-retaining quantity of water, and, during the drying cycle, to provide an open and malodour counteractant-releasing port.

\* \* \* \* \*